United States Patent
Zawacki et al.

(10) Patent No.: US 8,707,678 B2
(45) Date of Patent: *Apr. 29, 2014

(54) SYSTEM FOR AN ENGINE HAVING A PARTICULATE MATTER SENSOR

(75) Inventors: Garry Anthony Zawacki, Livonia, MI (US); Robert F. Novak, Farmington Hills, MI (US); Roberto Teran, Jr., Livonia, MI (US); Dave Charles Weber, Toledo, OH (US); Michiel J. Van Nieuwstadt, Ann Arbor, MI (US); Michael Hopka, Dearborn Heights, MI (US); William Charles Ruona, Farmington Hills, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 89 days.

This patent is subject to a terminal disclaimer.

(21) Appl. No.: 13/423,049

(22) Filed: Mar. 16, 2012

(65) Prior Publication Data

US 2012/0174564 A1    Jul. 12, 2012

Related U.S. Application Data

(63) Continuation of application No. 12/643,563, filed on Dec. 21, 2009, now Pat. No. 8,136,343.

(60) Provisional application No. 61/239,381, filed on Sep. 2, 2009.

(51) Int. Cl.
*F01N 3/00*    (2006.01)

(52) U.S. Cl.
USPC ............... 60/276; 60/274; 60/277; 60/295; 60/297; 60/311; 73/23.33; 73/28.01

(58) Field of Classification Search
USPC ........... 60/274, 276, 277, 286, 295, 297, 300, 60/311; 73/23.2, 23.31, 23.33, 28.01, 73/28.02
See application file for complete search history.

(56) References Cited

U.S. PATENT DOCUMENTS

| | | |
|---|---|---|
| 6,304,813 B1 | 10/2001 | Ikeda et al. |
| 6,432,168 B2 | 8/2002 | Schönauer |
| 7,526,914 B2 | 5/2009 | Nakano |
| 7,587,925 B2 * | 9/2009 | Wirth et al. ................ 73/1.02 |
| 7,765,792 B2 | 8/2010 | Rhodes et al. |
| 7,963,143 B2 | 6/2011 | Baumann et al. |
| 8,030,086 B2 | 10/2011 | Schmidt et al. |

(Continued)

OTHER PUBLICATIONS

"Applicants Statement of Related Art Known to Others", Statement as of Aug. 27, 2009, 1 Pg.

*Primary Examiner* — Binh Q Tran
(74) *Attorney, Agent, or Firm* — Julia Voutyras; Alleman Hall McCoy Russell & Tuttle LLP

(57) ABSTRACT

A system for improving operation of an engine having a particulate matter sensor is presented. The system may be used to improve engine operation during cold starts especially under conditions where water vapor or entrained water droplets are present in vehicle exhaust gases. In one embodiment, an engine controller that activates a heater of an exhaust gas sensor after an output of a particulate matter sensor exceeds a threshold value after an engine is started.

19 Claims, 7 Drawing Sheets

(56) References Cited

U.S. PATENT DOCUMENTS

| | | |
|---|---|---|
| 8,136,343 B2 * | 3/2012 | Zawacki et al. ............. 60/276 |
| 8,249,827 B2 * | 8/2012 | Nelson et al. ............. 702/183 |
| 8,261,540 B2 * | 9/2012 | Konstandopoulos et al. .. 60/297 |
| 8,490,465 B2 * | 7/2013 | Ante et al. ............. 73/23.2 |
| 2008/0087005 A1 | 4/2008 | Wahl et al. |
| 2008/0184774 A1 | 8/2008 | Aoki |
| 2011/0047978 A1 | 3/2011 | Zawacki et al. |
| 2011/0048106 A1 | 3/2011 | Zawacki et al. |

\* cited by examiner

SENSOR TEMPERATURE °C

SYSTEM FOR AN ENGINE HAVING A PARTICULATE MATTER SENSOR

CROSS-REFERENCE TO RELATED APPLICATIONS

The present application is a continuation of U.S. application Ser. No. 12/643,563, filed Dec. 21, 2009, which claims priority from U.S. Provisional Patent Application No. 61/239,381, entitled "SYSTEM FOR AN ENGINE HAVING A PARTICULATE SENSOR," filed Sep. 2, 2009, the disclosures of which are hereby incorporated by reference in its entirety and for all purposes.

FIELD

The present description relates to a system for improving operation of an engine having a sensor and a particulate filter. The system may be particularly useful for direct injection engines that are cold started.

BACKGROUND AND SUMMARY

One system for monitoring a sensor is provided in U.S. Pat. No. 7,526,914. This system presents a controller configured to calculate heat data corresponding to a heat budget in the exhaust pipe in close proximity to a sensor after an engine startup. The heat estimate is based upon an operating condition of the engine and a driving condition of a vehicle. The controller also makes a determination as to dryness inside the exhaust pipe based upon the heat data. Further, the power supply to the sensor heater is controlled based upon the result of the dryness determination.

The above-mentioned method can also have several disadvantages. Specifically, the system uses exhaust gas oxygen concentration and other variables to estimate when conditions in the vehicle exhaust system are dry enough to start heating an oxygen sensor. Since the sensor heater activation is related to an estimate of exhaust system conditions rather than to actual exhaust system conditions, the sensor heater may be activated earlier or later than is desired. As a result, the sensor may degrade at an undesirable rate if the heater is activated earlier than desired. On the other hand, if the sensor heater is activated later than desired, engine emissions may degrade.

The inventors herein have recognized the above-mentioned disadvantages and have developed a system for improving operation of an engine having a particulate matter sensor.

One embodiment of the present description includes a system for activating an exhaust sensor, comprising: an engine; an exhaust gas sensor; a particulate matter sensor; and a controller that activates a heater of said exhaust gas sensor when an output of said particulate matter sensor exceeds a threshold value after said engine is started.

By monitoring the output of a particulate matter sensor, the control of heater elements of other sensors located in the exhaust stream of an engine may be improved. For example, during an engine cold start, water condensate may form in the exhaust system as exhaust gases flow through the exhaust system. If a heating element of an oxygen sensor is activated before the water condensate leaves the exhaust system, performance of the oxygen sensor may degrade. On the other hand, if the oxygen sensor heater is activated later than desired, engine emissions may degrade. The inventors herein have developed a system where sensor heaters may be activated in relation to the output of a particulate matter sensor. Specifically, in one example, when the output of the particulate matter sensor provides a near impulse output, sensor heaters may be activated. The near impulse response of the particulate matter sensor results from a rapid change in the conductivity of the particulate matter sensor in the presence of water condensate. In one embodiment, when the particulate matter sensor response is below a second threshold, after exceeding a first threshold, the particulate matter sensor is indicating that water condensate is no longer present in the exhaust system; therefore, sensor heaters can be activated. In this way, the inventors herein have developed a way to activate exhaust system sensor heaters in response to exhaust system conditions rather than by inferences that may be less reliable.

The present description may provide several advantages. Specifically, the approach may improve engine emissions by allowing sensor heaters to bring sensors up to operating temperatures earlier and more reliably than systems that infer exhaust system conditions. Further, the system can reduce sensor degradation by reducing the possibility of activating sensor heaters before water in the exhaust system is vaporized.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The advantages described herein will be more fully understood by reading an example of an embodiment, referred to herein as the Detailed Description, when taken alone or with reference to the drawings, wherein.

DETAILED DESCRIPTION

Figure 1:
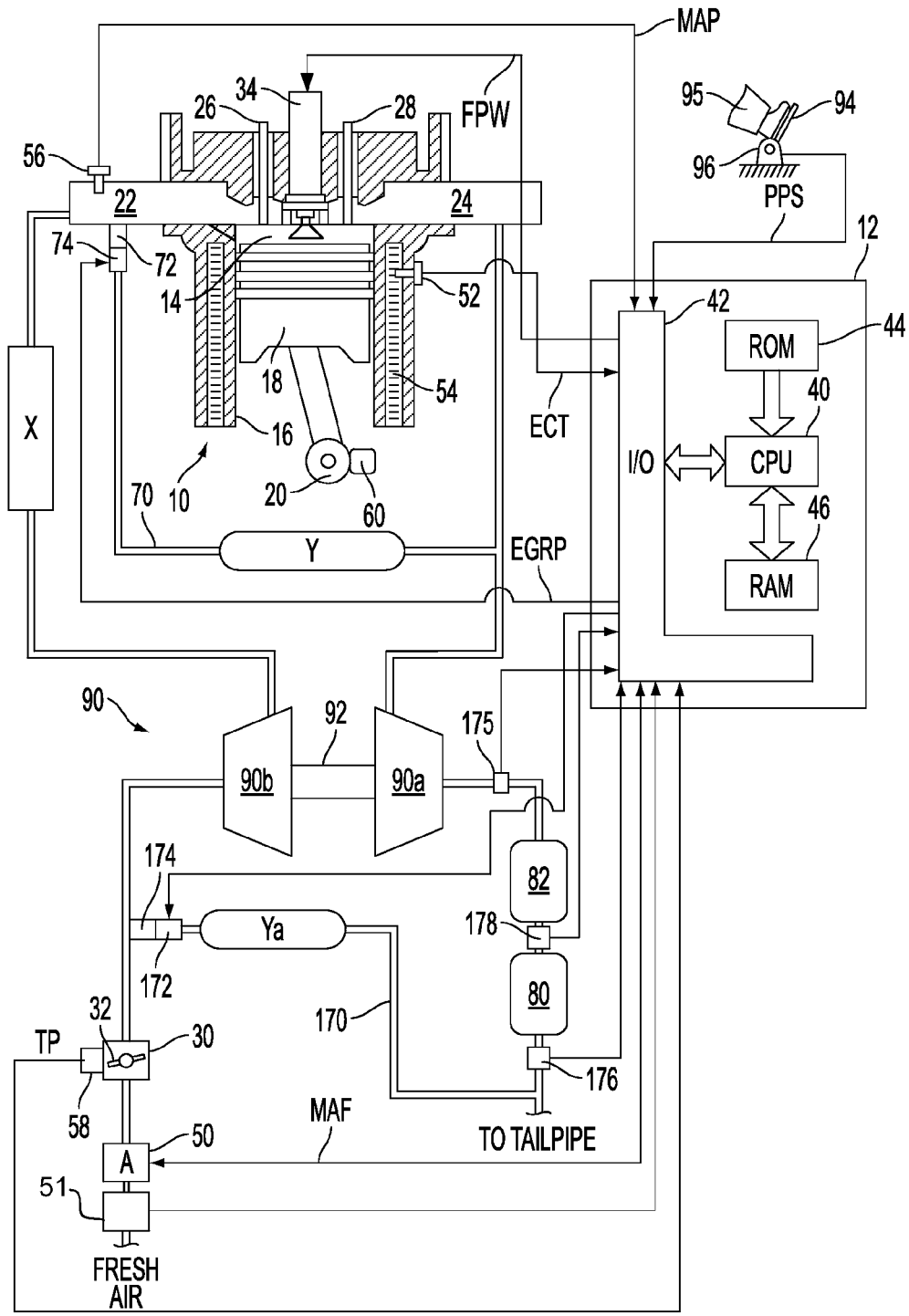
FIG. 1 is a schematic diagram of an engine.

FIG. 1 shows an exemplary embodiment of an engine system generally at 10. Specifically, internal combustion engine 10 comprises a plurality of cylinders, one cylinder of which is shown in FIG. 1. Engine 10 is controlled by electronic engine controller 12. Engine 10 includes combustion chamber 14 and cylinder walls 16 with piston 18 positioned therein and connected to crankshaft 20. Combustion chamber 14 communicates with an intake manifold 22 and an exhaust manifold 24 via respective intake valve 26 and exhaust valve 28.

Intake manifold 22 communicates with throttle body 30 via throttle plate 32. In one embodiment, an electronically controlled throttle can be used. In one embodiment, the throttle is electronically controlled to periodically, or continuously, maintain a specified vacuum level in intake manifold 22. Alternatively, throttle body 30 and throttle plate 32 may be omitted.

Combustion chamber 14 is also shown having fuel injector 34 coupled thereto for delivering fuel in proportion to the pulse width of signal (fpw) from controller 12. Fuel is delivered to fuel injector 34 by a conventional fuel system (not shown) including a fuel tank, fuel pump, and fuel rail (not shown). In the case of direct injection engines, as shown in FIG. 1, a high pressure fuel system is used such as a common rail system. However, there are several other fuel systems that could be used as well, including but not limited to EUI, HEUI, etc.

In the depicted embodiment, controller 12 is a conventional microcomputer, and includes a microprocessor unit 40, input/output ports 42, electronic memory 44, which may be an electronically programmable memory in this particular example, random access memory 46, and a conventional data bus.

Controller 12 receives various signals from sensors coupled to engine 10, including but not limited to: measurements of inducted mass airflow (MAF) from mass airflow sensor 50 coupled to the air filter [A on FIG. 1]; engine coolant temperature (ECT) from temperature sensor 52 coupled to cooling jacket 54; a measurement of manifold pressure (MAP) from manifold pressure sensor 56 coupled to intake manifold 22; a measurement of throttle position (TP) from throttle position sensor 58 coupled to throttle plate 32; intake air charge temperature sensor 51; and a profile ignition pickup signal (PIP) from Hall effect (or variable reluctance) sensor 60 proximate to crankshaft 20 indicating engine speed.

Engine 10 may include an exhaust gas recirculation (EGR) system to help lower $NO_x$ and other emissions. For example, engine 10 may include a high pressure EGR system in which exhaust gas is delivered to intake manifold 22 by a high pressure EGR tube 70 communicating with exhaust manifold 24 at a location upstream of an exhaust turbine 90a of a compression device 90, and communicating with intake manifold 22 at a location downstream of an intake compressor 90b of compression device 90. The depicted high pressure EGR system includes high pressure EGR valve assembly 72 located in high pressure EGR tube 70. Exhaust gas travels from exhaust manifold 24 first through high pressure EGR valve assembly 72, and then to intake manifold 22. An EGR cooler [shown at Y in FIG. 1] may be located in high pressure EGR tube 70 to cool recirculated exhaust gases before entering the intake manifold. Cooling is typically done using engine water, but an air-to-air heat exchanger may also be used.

Engine 10 may also include a low pressure EGR system. The depicted low pressure EGR system includes a low pressure EGR tube 170 communicating with exhaust manifold 22 at a location downstream of exhaust turbine 90a, and communicating with intake manifold 22 at a location upstream of intake compressor 90b. A low pressure valve assembly 172 is located in low pressure EGR tube 170. Exhaust gas in the low pressure EGR loop travels from turbine 90a through a catalytic device 82 (for example, a diesel oxidation catalyst and/or $NO_x$ trap) and a diesel particulate filter 80 before entering low pressure EGR tube 170. A low pressure EGR cooler Ya may be positioned along low pressure EGR tube 170.

High pressure EGR valve assembly 72 and low pressure EGR valve assembly 172 each has a valve (not shown) for controlling a variable area restriction in high pressure EGR tube 70 and low pressure EGR tube 170, which thereby controls flow of high and low pressure EGR, respectively.

Vacuum regulators 74 and 174 are coupled to high pressure EGR valve assembly 72 and low pressure EGR valve assembly 172, respectively. Vacuum regulators 74 and 174 receive actuation signals from controller 12 for controlling the valve positions of high pressure EGR valve assembly 72 and low pressure EGR valve assembly 172. In a preferred embodiment, high pressure EGR valve assembly 72 and low pressure EGR valve assembly 172 are vacuum actuated valves. However, any type of flow control valve or valves may be used such as, for example, an electrical solenoid powered valve or a stepper motor powered valve.

A particulate matter sensor 176 may be placed in the exhaust system between particulate filter 80 and the tailpipe to monitor particulate emissions. Likewise, a second particulate matter sensor 178 may be placed upstream of particulate filter 80. Particulate matter sensor 178 may be placed either between catalytic device 82 and particulate filter 80 (as depicted), or may be placed upstream of catalytic device 82. Particulate matter sensor 176 may be referred to herein as "downstream particulate matter sensor 176" and particulate matter sensor 178 may be referred to herein as "upstream particulate matter sensor 178." In one embodiment, particulate matter sensors may sense the accumulation of soot between two electrodes by a change in the impedance between the two electrodes.

Compression device 90 may be a turbocharger or any other such device. The depicted compression device 90 has a turbine 90a coupled in the exhaust manifold 24 and a compressor 90b coupled in the intake manifold 22 via an intercooler [shown at X in FIG. 1], which is typically an air-to-air heat exchanger, but could be water cooled. Turbine 90a is typically coupled to compressor 90b via a drive shaft 92. (This could also be a sequential turbocharger arrangement, single VGT, twin VGTs, or any other arrangement of turbochargers that could be used).

Further, drive pedal 94 is shown along with a driver's foot 95. Pedal position sensor (pps) 96 measures angular position of the driver actuated pedal. Further, engine 10 may also include exhaust air/fuel ratio sensors (not shown).

For example, either a 2-state EGO sensor or a linear UEGO sensor can be used. Either of these can be placed in the exhaust manifold 24, or downstream of devices 80, 82 or 90. It will be understood that the depicted diesel engine 10 is shown only for the purpose of example and that the systems and methods described herein may be implemented in or applied to any other suitable engine having any suitable components and/or arrangement of components.

Figure 2:
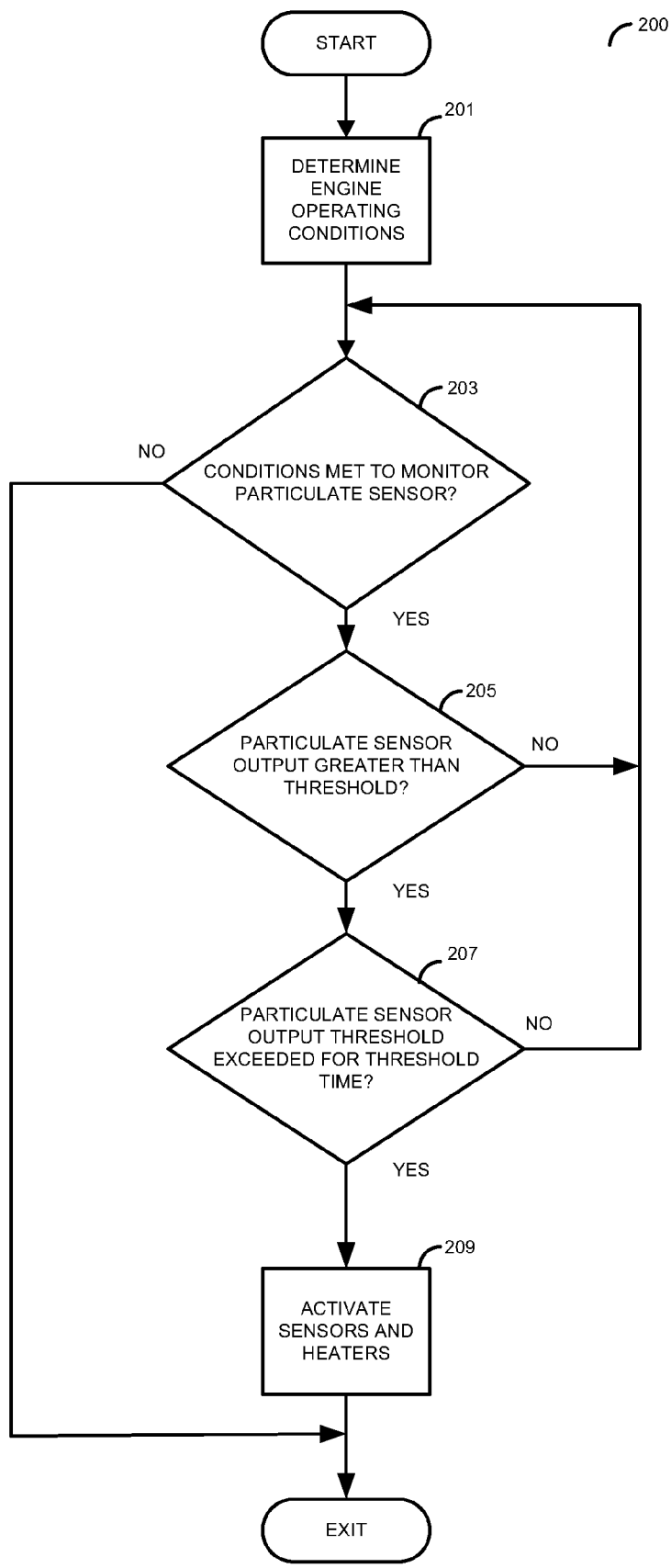
FIG. 2 is a flow chart of a sensor heater control routine that controls in relation to the output of a particulate matter sensor.

Referring to FIG. 2, a flow chart of a method for activating heaters of sensors located in an engine exhaust stream is shown. At 201, engine operating conditions are determined. In one example, engine coolant temperature, ambient temperature, ambient pressure, and time since engine stop may be determined. Of course, some embodiments may determine more or fewer engine conditions before engine start. After determining engine operating conditions, routine 200 proceeds to 203.

At 203, it is judged whether or not conditions are met to monitor the output of a particulate matter sensor. In one embodiment, the output of a particulate matter sensor may be monitored when the estimated exhaust gas temperature is between a first threshold value and a second threshold value. The exhaust gas temperature may be estimated from engine coolant temperature, engine load, injection timing, and the number of combustion events since engine start, for example.

In other embodiments, the particulate matter sensor may be monitored simply in relation to a time since start. Thus, the method of routine 200 may be executed during a first condition and bypassed or not executed during a second condition, the second condition different from the first condition. For example, routine 200 may be executed during a cold engine start and may not be executed during a warm engine start. Thus, routine 200 allows an engine controller to limit sensor heater current in response to the output of a particulate matter sensor. If conditions are met to monitor the output of a particulate matter sensor, routine 200 proceeds to 205. If conditions are not met, routine 200 proceeds to exit until it is executed again.

At 205, the output of a particulate matter sensor located in an exhaust stream is monitored. If the particulate matter sensor output exceeds a threshold value, routine 200 proceeds to 207. If not, routine 200 returns to 203. In another embodiment, the rate of change of the particulate matter sensor output may be determined. If the rate of change in the particulate matter sensor output is greater than a threshold, routine 200 proceeds to 207. If not, routine 200 returns to 203.

At 207, routine 200 judges if the particulate matter sensor output has exceeded a threshold value for more than a threshold amount of time. If so, routine 200 proceeds to 209. If not, routine 200 returns to 203. The threshold amount of time may be varied in relation to engine operating conditions if desired, or the threshold may be a constant. Further, the amount of time may be set to zero so that routine 200 can proceed to 209 if the particulate matter sensor output exceeds the threshold for a very brief period. In another embodiment, routine 200 may proceed to 209 if the particulate matter sensor output goes lower than a second threshold value after the output of the particulate sensor exceeds a first threshold for a first time since engine start. Otherwise, routine 200 returns to 203. Thus, routine 200 allows sensors and sensor heaters to be turned on based on different attributes of the particulate matter sensor output during an engine start. For example, heaters may be turned on at a rising or falling edge of an output signal from a particulate matter sensor. Further, sensors and/or sensor heaters may be activated when the output of a particulate matter sensor is above a threshold for a period of time. And of course, the period of time may be variable or constant.

In yet another embodiment, routine 200 may proceed to 209 in relation to other output attributes of a particulate matter sensor. In particular, the output of a particulate matter sensor may vary in response to engine operating conditions such that the particulate matter sensor provides additional information beyond an impulse-like response. For example, under some conditions the particulate matter sensor output may decay at a rate that may be related to exhaust gas temperature, ambient pressure, ambient humidity, or ambient temperature. In such conditions, the inflection point of the decay may be used to indicate when to activate other sensors or sensor heaters. Further, the rate of decay may be used to indicate when to activate other sensors or sensor heaters. For example, if the particulate matter sensor output decays at a rate that is greater than a threshold, other sensors or sensor heaters may be activated. In another example, if the particulate matter sensor output decays at a rate that is greater than a threshold, and then the rate of decay subsequently reduces to a rate that is less than a threshold rate of decay, then other sensors or sensor heaters may be activated when the particulate matter sensor output rate of decay is less than the threshold rate of decay. Further still, a routine may monitor both a rate of rise and rate of decay of an initial impulse-like response of a particulate matter sensor, and thus identify the first impulse-like response from the engine start.

Note that if the particulate matter sensor does not output a signal or if a signal is output, but below a threshold, during engine operation from a first condition to a second condition, the second condition different from the first condition, it may be judged that a particulate matter sensor shield is at least partially obstructed. For example, if an engine is started at a temperature of 18° C. and a particulate matter sensor does not output a signal by the time the engine reaches 70° C., it may be judged that a shield that protects the sensing element of the particulate matter sensor is at least partially obstructed from sensing exhaust gases.

At 209, routine 200 activates sensor heaters and/or sensors by supplying power to the sensors and/or sensor heaters. Sensor heaters may include but are not limited to oxygen sensor heaters, ammonia sensors, particulate sensor heaters, and NOx sensors. Power may be applied at full power or power may be gradually increased in relation to the output of the particulate matter sensor. In one embodiment, a heater voltage is modulated to an oxygen sensor heater. The voltage is begins at a low duty cycle (e.g., 10%) and is ramped to a higher duty cycle (e.g., 100%) before the heater is deactivated by setting the heater duty cycle to 0% in response to engine operating conditions.

It should be noted that the method of FIG. 2 can be applied to more than a single particulate matter sensor so that activation of different sensors and sensor heaters may be accomplished relative to different particulate matter sensors. For example, sensors and sensor heaters located upstream of a first particulate matter sensor can be activated in response to the output of a first particulate matter sensor while sensors and sensor heaters located between the first particulate matter sensor and a second particulate matter sensor are activated in response to a second particulate matter sensor located downstream of the first particulate matter sensor. Further, routine 200 allows the engine controller to activate a sensor heater after output of a particulate matter sensor exceeds said threshold value for the first time since the engine was last stopped.

Figure 3:
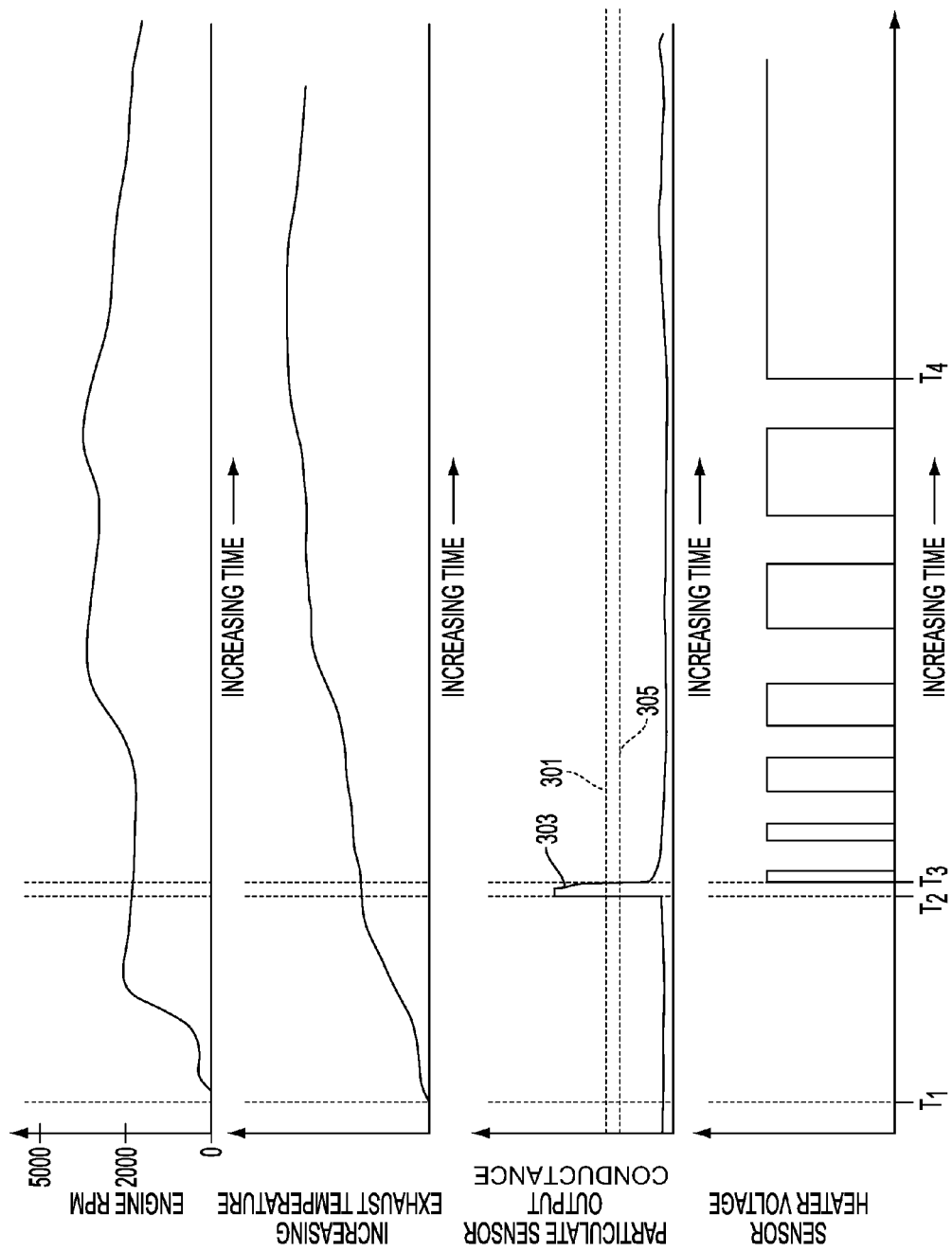
FIG. 3 is an example plot of example signal of interest during an engine start.

Referring now to FIG. 3, it shows some signals or interest during an example engine cold start. For each of the plots, time begins from zero on the left side of the plot and increase to the right side of each plot.

In the upper plot, an example of engine speed during engine start is illustrated. The engine starts from rest at time $T_1$ and approaches 2000 RPM as it starts. Later in time, engine speed may be related to driver demand torque as time progresses from left to right. In this example, engine speed increases and decreases with driver demand.

In the plot second from the top of FIG. 3, example exhaust gas temperature is plotted. The exhaust gas temperature begins at ambient temperature before the engine is started and then increases. The exhaust temperature can be related to engine speed, engine load, and number of combustion events from engine start. In this example, exhaust gas temperature increases for approximately two-thirds of the plot and then levels off. Of course, actual exhaust gas temperatures are expected to vary depending on starting conditions and engine operating conditions.

In the plot third from the top of FIG. 3, an example output of a particulate temperature sensor is shown. This plot represents the change in electrical conductance of a particulate sensor. Initially, the sensor output is low and then abruptly increases at approximately one-fifth of the way through the plot. The increase corresponds to an increase of conductance from water droplets that may entrain on the sensing element. The particulate matter sensor output resembles an impulse response, but the duration of the response may vary depending on engine operating conditions and ambient conditions.

Accordingly, activation or sensors or sensor heaters may be related to the impulse duration, the start of the impulse, or when the level of the impulse-like signal falls below a threshold amount. Further, the activation of other sensors and sensor heaters may be related to the position in the exhaust system where the particulate sensor is located. For example, sensors and heaters may be activated after a particulate matter sensor outputs a voltage above a threshold for more than 0.1 seconds when the particulate sensor is located downstream of the sensor or heater to be activated. The horizontal dashed line 301 represents a first threshold level that may be used to judge whether or not water condensate is present in the exhaust system. If the particulate matter sensor output exceeds the threshold level, it may be judged that water condensate is in the exhaust system. Thus, at time $T_2$ the particulate matter sensor indicates water condensate is present in the exhaust system.

At $T_3$, the particulate matter sensor output begins to decay below a second threshold 305 and indicates that water condensate is no longer present in the exhaust system, at least where the particulate matter sensor is mounted. In one example, routine 300 determines that water condensate is no longer present in the exhaust system upstream of where the particulate matter sensor is located because temperatures may assumed to be warmer upstream of the particulate matter sensor location. In particular, at higher exhaust temperatures, the dew point temperature is exceeded so that water condensate will not form in the exhaust. Therefore, in systems that employ multiple particulate matter sensors, sensors and sensor heaters that are upstream of a particulate matter sensor that indicates water condensate is no longer in the exhaust can be activated. For example, if first and second particulate matter sensors are positioned in an exhaust system, and the first particulate matter sensor is located upstream of second particulate matter sensor, sensors and sensor heaters located upstream of the first particulate matter sensor can be activated after the first particulate matter sensor outputs an impulse similar to impulse 303. Sensors and sensor heaters located downstream of the first particulate matter sensor but upstream of the second particulate matter sensor may be activated after the second particulate matter sensor outputs an impulse similar to impulse 303. Sensors and sensor heaters may be activated at the first or second threshold depending on system configuration and objectives. Thus, sensors and sensor heaters may be activated as the exhaust gas temperature exceeds the dew point temperature at the particular sensor location in the exhaust system.

Note that the actual point in time where water condensate is no longer present in the exhaust system may be deemed at any point after the particulate matter sensor begins to decay at $T_3$. The description of FIG. 2 provides an explanation of several different options. Also note that the lack of an impulse-like change in conductance or resistance similar to 303 can be used to indicate a degraded sensor or a plugged sensor shield.

The bottom plot illustrates an example of oxygen sensor heater control. Between $T_1$ and $T_3$ the oxygen sensor heater is off. At $T_3$, the oxygen sensor is turned on by applying a voltage to the oxygen sensor heater. The voltage is periodically cycled on and off so that the oxygen sensor is heated gradually. Heating the sensor gradually may reduce heater and sensor degradation. Note that the plot is only illustrative and not meant to limit the scope of heater control. Heater voltage may be applied at a higher frequency and different duty cycle than that which is illustrated without departing from the scope or intent of the description. At $T_4$, the heater voltage is applied at 100% duty cycle.

Figure 4:
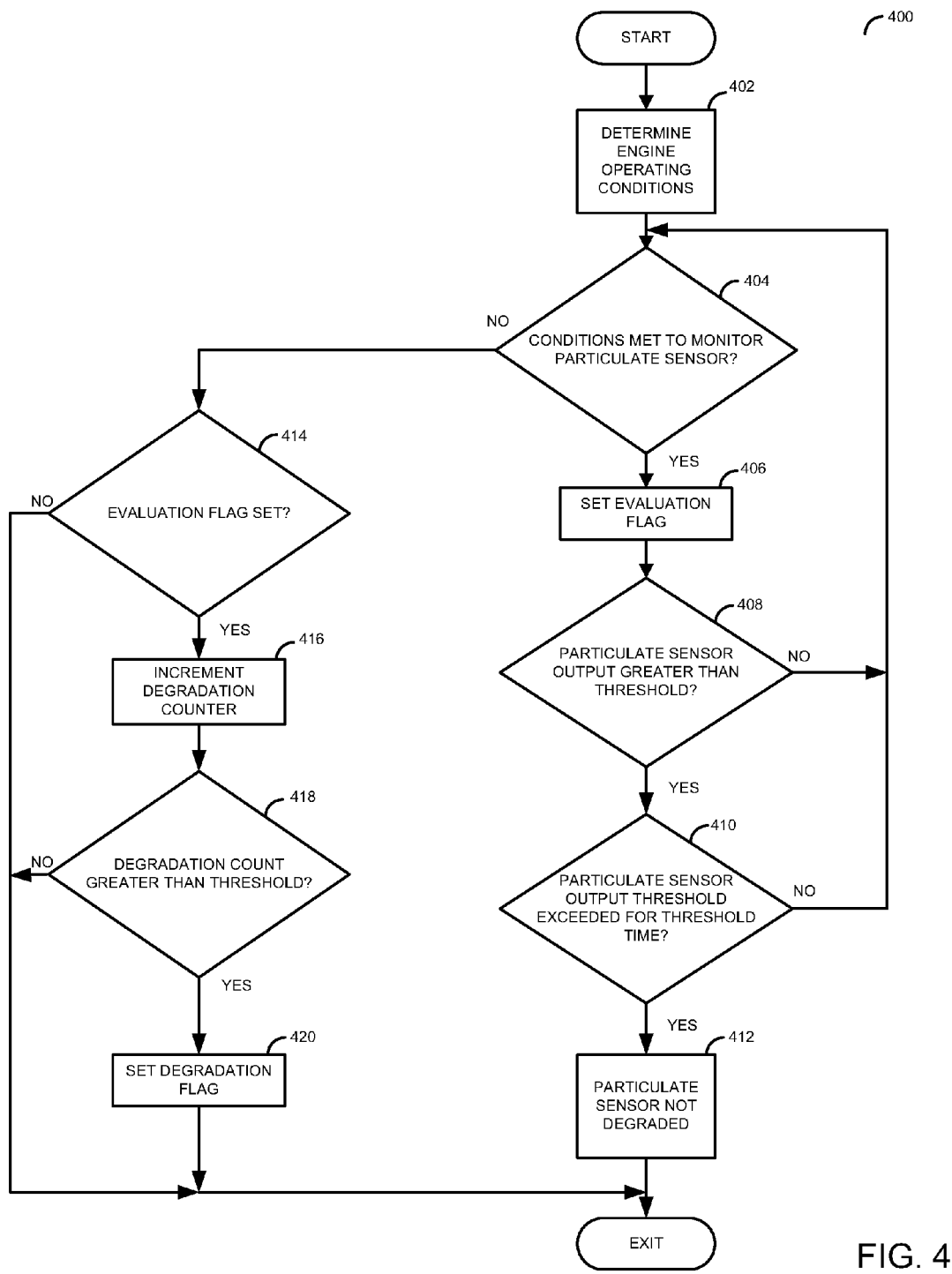
FIG. 4 is a flow chart of a particulate matter sensor evaluation routine.

Referring now to FIG. 4, a flow chart of a method to diagnose whether or not a particulate matter sensor is functioning as desired is shown. The method can be useful for determining whether an open in the particulate matter sensor circuit exists or whether a sensor shield may be plugged. The method looks for a brief spike or impulse at the output of a particulate matter sensor which indicates increased particulate matter sensor conductance that may be observed when an engine is cold started, as previously shown in FIG. 3. Conductance of the particulate matter sensor may increase during a cold start as water vapor from engine exhaust impinges on the particulate matter sensor substrate and condenses as the exhaust gas temperature cools below the dewpoint. The water vapor in the exhaust may be formed from exhaust byproducts or from other water that has condensed in the exhaust system. The exhaust system temperature may gradually increase so that the water evaporates from the substrate and the conductance decreases; thereby, decreasing the particulate matter sensor output. Thus, the sensor can be expected to provide an output under certain engine operating conditions. By monitoring the output of the particulate matter sensor during cold start operating conditions, an evaluation of sensor operation may be made without additional circuitry or without disturbing system operation. During other engine operating conditions the particulate matter sensor output may not be monitored so that the engine controller can be released for other tasks.

At 402, engine operating conditions are determined. In one example, engine coolant temperature, ambient temperature, ambient pressure, and time since engine stop may be determined. Of course, some embodiments may determine more or fewer engine conditions before engine start. After determining engine operating conditions, routine 400 proceeds to 404.

At 404, it is judged whether or not conditions are met to monitor the output of a particulate matter sensor. In one embodiment, the output of a particulate matter sensor may be monitored when the estimated exhaust gas temperature is between a first threshold value and a second threshold value, the dewpoint between the first threshold value and the second threshold value. The exhaust gas temperature may be estimated from engine coolant temperature, engine load, injection timing, and the number of combustion events since engine start, for example. In other embodiments, the particulate matter sensor may be monitored simply in relation to a time since start. Thus, the method of routine 400 may be executed during a first condition and bypassed or not executed during a second condition. If conditions are met to monitor the output of a particulate matter sensor, routine 400 proceeds to 406. If conditions are not met, routine 400 proceeds to 414.

At 406, a flag is set to establish that an evaluation of a particulate matter sensor has been initiated. The flag is used in part to determine whether or not a particulate matter sensor degradation indication should be made. Routine 400 then proceeds to 408.

At 408, the output of a particulate matter sensor located in an exhaust stream is monitored. If the particulate matter sensor output exceeds a threshold value, routine 400 proceeds to 410. Alternatively, routine 400 may proceed to 410 after the particulate matter sensor output exceeds a first threshold and then falls below a second threshold. In another embodiment, the rate of change of the particulate matter sensor output may be determined. If the rate of change in the particulate matter sensor output is greater than a threshold, routine 400 proceeds to 410. In still another embodiment, if the change in conductance is greater than a threshold amount or if sensor conductance is greater than a threshold amount, routine proceeds to

410. If substantially no change (e.g., less than 5% of full scale output) in sensor output is observed by way of a change in conductance or by an output of voltage or current after an engine temperature has exceeded a dewpoint temperature, routine 400 returns to 404.

At 410, routine 400 judges if the particulate matter sensor output has exceeded a threshold value for more than a threshold amount of time. If so, routine 400 proceeds to 412. If not, routine 400 returns to 404. The threshold amount of time may be varied in relation to engine operating conditions if desired, or the threshold may be a constant. In another embodiment, routine 400 may proceed to 412 if the particulate matter sensor output goes lower than a second threshold value after the output of the particulate sensor exceeds a first threshold for a first time since engine start. Otherwise, routine 400 returns to 404.

In yet another embodiment, routine 400 may proceed in relation to other output attributes of a particulate matter sensor. In particular, the output of a particulate matter sensor may vary in response to engine operating conditions such that the particulate matter sensor provides additional information beyond the impulse-like response. For example, under some conditions the sensor output may decay at a rate that may be related to exhaust gas temperature, ambient pressure, ambient humidity, or ambient temperature. In such conditions, the inflection point of the decay may be used to indicate when to activate other sensors or sensor heaters. Further, the rate of decay may be used to indicate when to activate other sensors or sensor heaters. For example, if the particulate matter sensor output decays at a rate that is greater than a threshold, other sensors or sensor heaters may be activated. In another example, if the particulate matter sensor output decays at a rate that is greater than a threshold and then the rate of decay subsequently reduces to a rate that is less than a threshold rate of decay, then other sensors or sensor heaters may be activated when the particulate matter sensor output rate of decay is less than the threshold rate of decay.

At 412, routine 400 resets to zero the evaluation flag that was set in step 406 and indicates that the particulate matter sensor is not degraded beyond a threshold level. Routine 400 proceeds to exit after 412.

At 414, routine 400 determines if the particulate matter sensor test flag was set in step 406. If not, routine 400 exits. If so, routine 400 proceeds to 416. If the test flag was set at 406 and conditions for monitoring the particulate matter sensor are no longer met without the particulate matter sensor outputting a signal, routine 400 determines that the particulate matter sensor has degraded in some manner and proceeds to 416.

At 416, a degradation counter is incremented. However, if a subsequent particulate matter sensor evaluation indicates a desired signal from the particulate matter sensor, the counter may be reset or decremented at 412.

At 418, routine 400 determines if the degradation counter has reached a threshold level. If so, an indication to the vehicle operator or another engine system may be made at 420. After indicating degradation at 420 the particulate matter sensor test flag that was set at 406 is reset. If the degradation counter has not reached a threshold level, routine 400 proceeds to exit after resetting the particulate matter sensor test flag that was set at 406.

Thus, routine 400 can asses degradation of particulate matter sensors between first and second exhaust gas temperatures and indicate sensor degradation if the output of the particulate sensor does not exceed a threshold while engine exhaust gases are between the first and second exhaust gas temperatures. Further, an indication of degradation of a particulate matter sensor can be output after a plurality of engine starts so that an indication of degradation is not output for a single engine start where conditions may deviate from conditions where an output by the particulate sensor might be expected.

Note that the method of FIG. 4 may be applied to more than one sensor so that the outputs of different sensors may be compared during a single engine start. For example, for an engine having two separate exhaust passages, the output of one sensor during an engine start can be compared to the output of another particulate matter sensor located in a second different exhaust passage. If one particulate matter sensor indicates an output during a start, and the other particulate matter sensor doesn't indicate an output during the start or remains substantially unchanged (e.g., changes less that 5% of full scale), an indication of degradation of the sensor not outputting an impulse-like response may be given. Alternatively, an indication of a plugged sensor shield of the sensor having an output that does not change may be provided. If both sensors output impulse-like responses both sensors may be judged not degraded beyond a desired amount.

When the method of FIG. 4 is applied to an engine system having more than one particulate matter sensors, the particulate matter sensors may be located in different branches of the engine exhaust system. For example, a first particulate matter sensor may be located in a first branch and a second particulate matter sensor may be located in a second branch. Alternatively, the first particulate matter sensor and the second particulate matter sensor may be located in the same exhaust passage where the first particulate sensor is located upstream of the second particulate matter sensor. Where one particulate matter sensor is located downstream of the other particulate matter sensor, it is expected that the output of one sensor may change before the output of the other sensor. In such cases, assessment and indication of sensor degradation may be delayed until outputs from both sensors may be expected. Alternatively, the comparison of an output from said first particulate matter sensor to an output of said second particulate matter sensor may be conducted after the output of said first particulate matter sensor exceeds a threshold level and after the output of the first particulate matter sensor falls below a second threshold level. Further, the timing of the output of one or the other particulate matter sensor may be shifted in time so that the sensor outputs can be compared. For example, if an upstream particulate sensor changes conductivity at $T_1$ and downstream particulate sensor changes conductivity at $T_2$, the difference in time between $T_1$ and $T_2$ being 0.25 seconds, then the recorded output of $T_2$ can be shift forward in time by 0.25 seconds so that a relevant comparison between sensors may be made.

Figure 5:
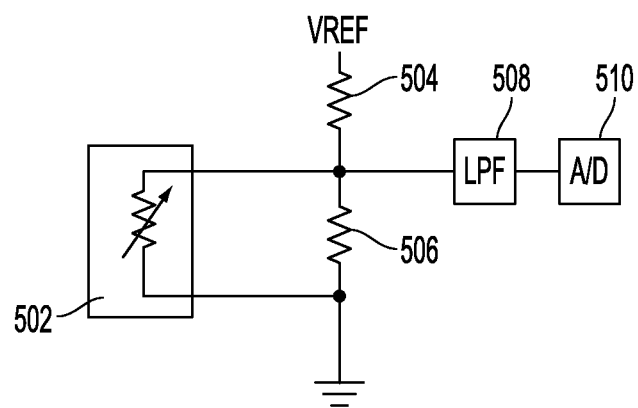
FIG. 5 shows an example particulate matter sensor evaluation circuit.

Referring now to FIG. 5, a circuit for diagnosing a short circuit in the particulate matter sensor is shown. Pull-up resistor 504 creates a voltage after low pass filter 508 that allows measurement the particulate matter sensor conductance using a transfer function and A/D convertor, for example. The pull-up resistor is sized based on the number of squares of particulate matter collection surface. Pull-down resistor 506 creates a 4.5×VREF signal when the particulate matter sensor is open circuit. The particulate matter sensor appears as an open circuit often because it has high impedance. However, drift of the pull-up resistance may also be detected since a signal that is not close to 4.5×VREF may be observed. As such, a controller could set a flag to check the controller hardware. In addition, if a wire supplying heater power to the particulate matter sensor degrades, a higher voltage may be observed at the controller. The circuit of FIG. 5 allows the particulate matter sensor to be diagnosed between a first and second threshold voltage level created by the circuit. For example, a voltage greater than 4.5×VREF may indicate particulate matter sensor degradation. And, a voltage that is much less than 4.5×VREF may not occur immediately after sensor regeneration (e.g., combusting soot on the sensor) because the resistance of the element is high. Consequently, indications for voltage higher than expected and for voltage lower than expected after particulate matter sensor regeneration may be provided by monitoring the voltage between pull-up resistor 504 and pull-down resistor 506.

Figure 6:
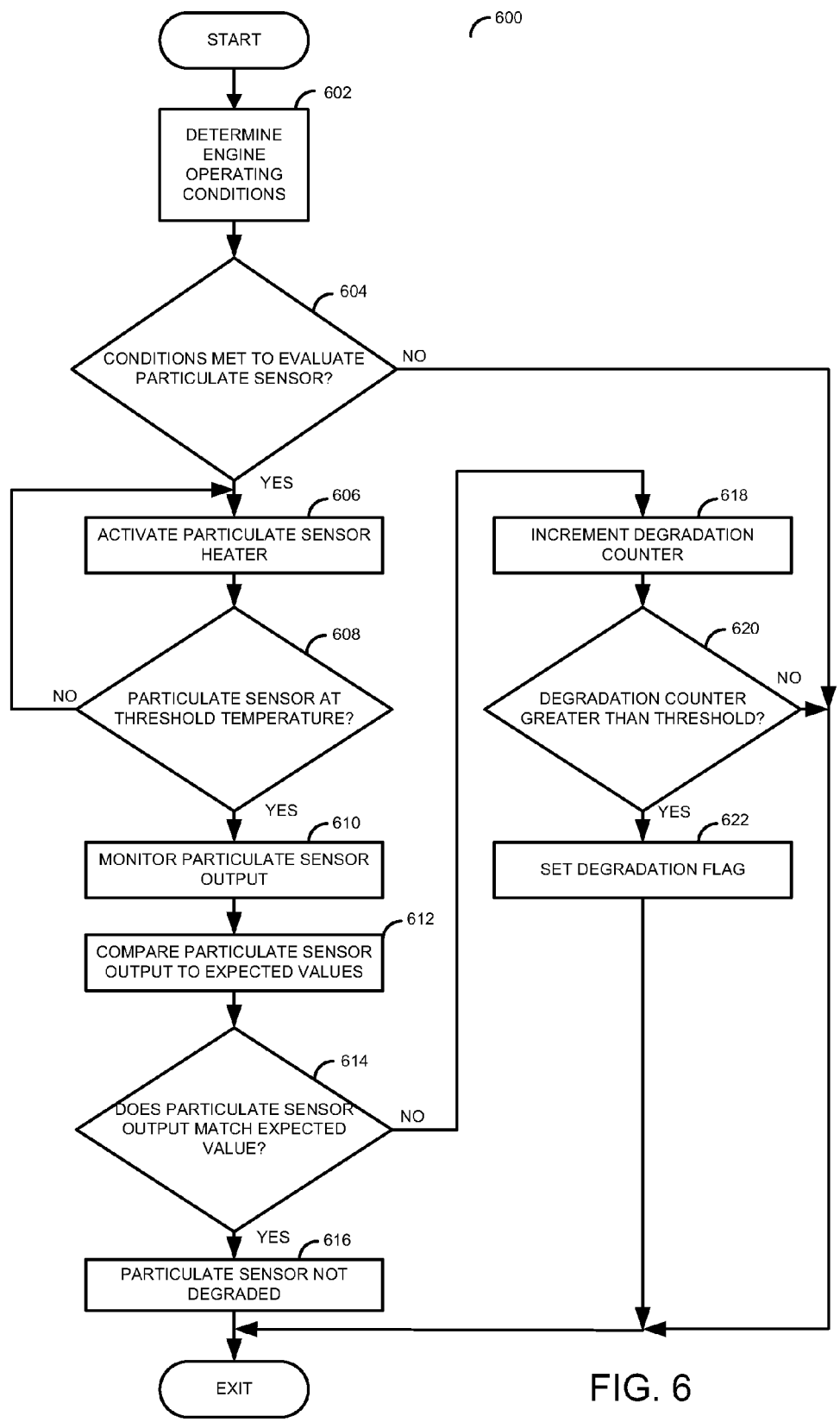
FIG. 6 is a flow chart of a particulate matter sensor evaluation routine.

Referring now to FIG. 6, a flow chart of an alternate method to diagnose whether or not a particulate matter sensor is functioning as desired is shown. The method heats a particulate matter sensor and looks for a change in the sensor output. For example, the sensor conductance can change so that additional current may flow through the sensor. Sensor output can change during sensor heating because the heating may allow leakage current to increase between the particulate matter sensor electrodes, thereby increasing the particulate matter sensor output.

At 602, engine operating conditions are determined. In one example, engine coolant temperature, ambient temperature, ambient pressure, and time since engine stop may be determined. By assessing engine operating conditions, routine 600 may initiate a particulate matter sensor evaluation when the evaluation is likely to have less effect on engine operation. After determining engine operating conditions, routine 600 proceeds to 604.

At 604, it is judged whether or not conditions are met to initiate evaluation of particulate matter sensor degradation. In one embodiment, the particulate matter sensor may be evaluated when the engine is not operating. For example, a particulate matter sensor may be evaluated after key-on while glow-plugs are being heated. In another embodiment, the particulate matter sensor may be evaluated when engine out particulates are expected to be low. For example, a particulate matter sensor may be evaluated when engine load is low and when engine speed is low. Thus, the method of routine 600 may be executed during a first condition and bypassed or not executed during a second condition. If conditions are met to evaluate a particulate matter sensor, routine 600 proceeds to 606. If conditions are not met, routine 600 proceeds to exit.

At 606, the particulate matter sensor heater is activated. The particulate matter sensor heater may be controlled to a desired temperature by adjusting voltage or current supplied to the heater. In one embodiment, the heater may be subject to a particular current profile so that the particulate matter sensor output will exhibit an expected response or value of current or voltage. The current profile may be stored in the memory of an engine controller and indexed as a function of time since start of evaluation. After activating the particulate matter sensor heater routine 600 proceeds to 608.

In addition, a timer may be started at 606 for a purpose of inferring the resistance of the particulate matter sensor heater. It may be desirable under some conditions to measure or calculate the amount of time that it takes for a heater to oxidize particulate matter on the particulate matter sensor. By determining the time it takes to lower conductance of a particulate matter sensor, particulate matter sensor resistance may be inferred. For example, if the time it takes to regenerate a particulate matter sensor increases, it may be determined that the heater circuit is an open circuit so that a diagnostic code or flag may be set to indicate particulate heater degradation. As a result, the particulate matter sensor heater resistance can be monitored without adding the expense of separate circuitry for determining particulate matter sensor heater resistance.

At 608, routine 600 determines whether or not the particulate matter sensor is at a threshold temperature before assessing the particulate matter sensor output. In one example, routine 600 determines if the substrate of the particulate matter sensor has reached a threshold temperature. In another example, routine 600 determines if the particulate matter sensor substrate has reached a temperature requested by a current profile in step 606. In one example, a first order model can be used to estimate the particulate substrate temperature. For example, using the heater current as an input, substrate temperature can be estimated. If the particulate matter sensor is at the desired temperature, routine 600 proceeds to 610. If not, routine 600 proceeds back to 606 where the particulate matter sensor heater temperature is controlled to the desired temperature.

At 610, routine 600 monitors the output of the particulate matter sensor. The sensor output may be monitored in a variety of ways and the particular method for monitoring the particulate matter sensor output may accordingly vary. In one embodiment, the voltage output from the particulate matter sensor is monitored by an engine controller. The particulate matter sensor output may be monitored while current is applied to the particulate matter sensor or for a period of time after current is withdrawn from the particulate matter sensor. After monitoring the particulate matter sensor output, routine 600 proceeds to 612.

At 612, routine 600 compares the particulate matter sensor output to expected values. In one embodiment, the particulate matter sensor output is compared to empirically determined values that are stored in memory of an engine controller. Further, in one embodiment, the particulate matter sensor may be evaluated and the evaluation results stored in memory to use as a basis for comparison with later particulate matter sensor evaluations. Thus, for example, particulate matter sensor heater current can be increased so that leakage current between the positive and negative electrodes of the particulate matter sensor increases. However, if the leakage current is less than a threshold value, it may be judged that the particulate matter sensor is degraded. In this way, the particular response of a particular sensor may be used as a basis for subsequent particulate matter sensor tests. This allows routine 600 to adapt to sensor variations that may be related to manufacturing or other sources.

The comparison of particulate matter sensor output to other sources or references may be accomplished in a variety of ways. In one example, the data of an evaluation may be subtracted by reference data to create an error. The error may be summed over the evaluation interval to create a value that may be assessed against a predetermined threshold value. If the value deviates from the threshold value by more than a prescribed amount, degradation may be determined. Thus, the particulate matter sensor regeneration heater may be activated, and if the resistance of the particulate matter sensor may decreases, or the conductance increases, it may be judged that the particulate matter has been degraded by conductive material, such as a metal. In one example, a regeneration heater may be activated and increase the temperature of a substrate of a particulate matter sensor above a threshold temperature. This method allows a controller to assess deposition of a conductive material on a particulate matter sensor in response to a resistance or conductance of said particulate matter sensor. This particular method may be performed whether or not the engine is operating or stopped.

In another embodiment, the particulate matter sensor output may be evaluated at specific intervals during the evaluation period. For example, particulate matter sensor output may be evaluated or monitored after a first amount of current is applied for a first period of time, and again after a second amount of current is applied for a second period of time. After comparing the particulate matter sensor output to expected values, routine 600 proceeds to 614.

In addition, if a timer is started at 606, the timer is stopped at 612. The sensor conductance or resistance can be compared to a function and if the conduction is less than a threshold level, then in one example, it may be judged that there is an open circuit and a particulate matter sensor regeneration heater degradation flag may be set. On the other hand, if the resistance of a particulate matter sensor is greater than a threshold level, it may be judged that there is an open circuit and a particulate matter sensor regeneration heater regeneration heater degradation flag may be set. Thus, the engine controller can infer the resistance of the particulate matter sensor regeneration heater. In another example, the controller may determine an amount of time for the conductance or resistance of said particulate matter sensor to go from a first threshold value to a second threshold value. For example, if a constant voltage is applied to the particulate matter sensor, the particulate matter sensor conduction may change from a first level of 0.0001 mhos to 0.001 mhos at second level. Or in the alternative, the resistance may go from 10,000 ohms to 1,000 ohms.

At 614, routine 600 determines whether to proceed to 616 or 618. If the particulate matter sensor output matches the expected value routine 600 proceeds to 616. If not, routine 600 proceeds to 618.

At 616, routine 600 indicates that the particulate matter sensor has not degraded by more than an allowable amount. Further, if degradation had been observed or detected during a previous evaluation, the degradation counter of 618 may be reset or decremented before routine 600 exits.

At 618, routine 600 increments a degradation counter and proceeds to 620. At 620, routine 600 determines if the degradation counter has reached a threshold level. If so, an indication to the vehicle operator or another engine system may be made at 622. If the degradation counter has not reached a threshold level, routine 600 proceeds to exit.

In another embodiment used with the method of FIG. 6, a resistor layer may be added between the electrodes of the particulate matter sensor. A resistive layer between the electrodes allows a sensor with minor degradation to the sensing electrode to be considered passing. A discrete resistor bridging the ends of the particulate matter sensor electrodes will flag any degradation to the electrode as sensor degradation. A resistor layer with a known temperature coefficient can be used to make the leakage current directly proportional to the sensor element temperature. The resistor material can be specified such that at standard particulate matter sensor operating temperatures (100 to 400° C.) the resistance would change little as the temperature varies; however, at the elevated temperatures seen during or after sensor heating, the resistor would have a strong temperature dependence. This arrangement facilitates a sensor output that is proportional to temperature only during heating. And, it allows for the change in sensor resistance to be used for evaluation with little influence on normal measurements. The resistor also makes the open/short circuit test much easier for the particulate matter sensor because are few conditions where the sensor is normally open circuit or high resistance.

Figure 7:
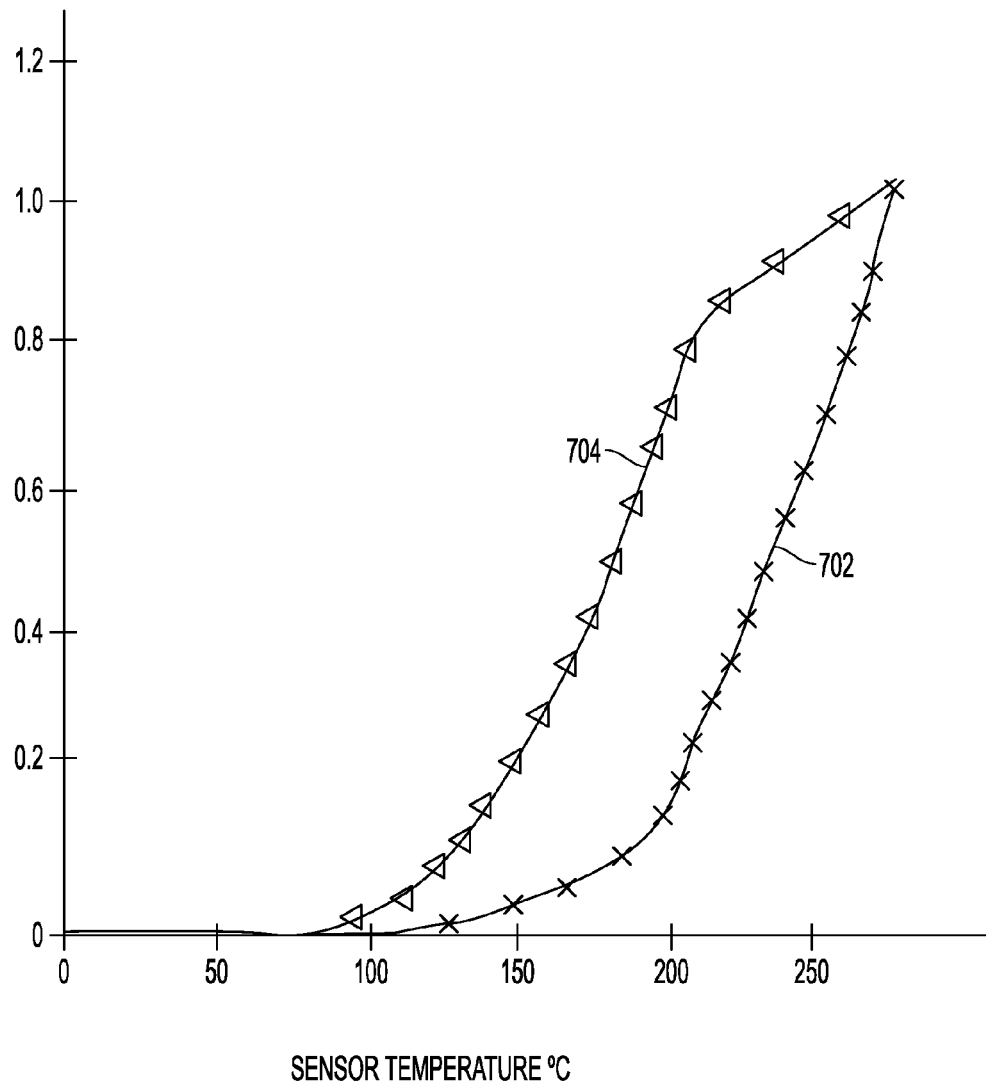
FIG. 7 is a plot of an example particulate matter sensor output.

Referring to FIG. 7, an example of expected output from a particulate matter sensor is shown. Output voltage is plotted against particulate matter sensor substrate temperature in degrees Celsius. Curve 702 represents the particulate matter sensor output when sensor temperature is increasing. Curve 704 represents the particulate matter sensor output when sensor temperature is decreasing. Such data may be the basis for evaluating particulate matter sensor degradation in the method of FIG. 6.

As will be appreciated by one of ordinary skill in the art, routines described in FIGS. 2, 4, and 6 may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the objects, features, and advantages described herein, but is provided for ease of illustration and description. Although not explicitly illustrated, one of ordinary skill in the art will recognize that one or more of the illustrated steps or functions may be repeatedly performed depending on the particular strategy being used.

This concludes the description. The reading of it by those skilled in the art would bring to mind many alterations and modifications without departing from the spirit and the scope of the description. For example, I3, I4, I5, V6, V8, V10, and V12 engines operating in natural gas, gasoline, diesel, or alternative fuel configurations could use the present description to advantage.

The invention claimed is:

1. A system for activating an exhaust sensor, comprising:
an engine;
an exhaust gas sensor;
a particulate matter sensor; and
a controller that activates a heater of said exhaust gas sensor after an output of said particulate matter sensor exceeds a threshold value after said engine is started, the heater activation including ramping heater power in relation to the output of the particulate matter sensor.

2. The system of claim 1 wherein said controller activates said heater after said particulate matter sensor exceeds said threshold value for a first time since the engine was last stopped.

3. The system of claim 1 wherein said controller activates said heater during the first condition and does not activate said heater during a second condition.

4. The system of claim 3 wherein said first condition is a cold start and wherein said second condition is a warm start, and wherein said controller indicates at least a partially obstructed shield element of said particulate matter sensor when said output of said particulate matter sensor is less than a threshold.

5. The system of claim 1 wherein said controller observes the output of said sensor between a first condition and a second condition.

6. The system of claim 5 wherein said first condition is a first temperature and wherein said second condition is a second temperature, said second temperature greater than said first temperature.

7. The system of claim 1 wherein said controller limits said activation of said heater until said output of said particulate matter sensor exceeds said threshold value for a threshold period of time.

8. The system of claim 1 wherein said particulate matter sensor has a resistive element for determining a presence of particulate matter.

9. A method for activating a heater of a particulate matter sensor, comprising:
starting an engine; and
activating a heater of an exhaust gas sensor positioned upstream of a particulate matter sensor after an impulse response is generated by the particulate matter sensor, the impulse response including an output spike greater than a threshold over a duration, the activation based on the duration.

10. The method of claim 9 wherein said activation of said heater is related to a period of engine operation when exhaust gases from said engine are at a temperature between a first temperature and a second temperature.

11. The method of claim 9 wherein activation of said heater includes supplying said heater with a modulated current.

12. The method of claim 11 wherein said modulated current begins at a first level of modulation, proceeds to a second level of modulation, and proceeds to a third level of modulation.

13. The method of claim 12 wherein said first level of modulation is less than a 100% duty cycle, said second level of modulation is greater than said first level of modulation and less than a 100% duty cycle, and said third level of modulation is less than a 20% duty cycle.

14. A method for activating a heater of a particulate matter sensor, comprising:
    starting a diesel engine during a first condition;
    activating a heater of an exhaust gas sensor at a first time since engine start in response to an output of a particulate matter sensor exceeding a threshold value; and
    starting the diesel engine during a second condition and activating the heater of the exhaust gas sensor at a second time since engine start, the second time an earlier time since engine start than the first time.

15. The method of claim 14 wherein said first condition is a cold start and said second condition is a hot start.

16. The method of claim 14 wherein said activating said heater during engine start during the second condition includes activating the heater of the exhaust gas sensor without relying on the output of the particulate matter sensor.

17. The method of claim 14 wherein said activating said heater is related to an amount of time said output of said particulate matter sensor exceeds said threshold value.

18. The method of claim 17 wherein said activating said heater occurs after said amount of time exceeds a threshold.

19. The method of claim 14 wherein activation of said heater includes supplying said heater with a modulated current.

* * * * *